United States Patent
Bedard et al.

(10) Patent No.: US 6,455,459 B1
(45) Date of Patent: Sep. 24, 2002

(54) ANTIMONY CATALYST COMPOSITIONS

(75) Inventors: Thomas Craig Bedard; Brian Terry Keen, both of Charleston; Bradley Allen Sleadd, Nitro, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/442,565

(22) Filed: Nov. 18, 1999

(51) Int. Cl.⁷ ................................................ B01J 31/00
(52) U.S. Cl. ........................ 502/152; 502/150; 502/169; 502/224; 423/87; 423/466
(58) Field of Search ............................... 502/150, 152, 502/169, 224; 423/87, 466

(56) References Cited

U.S. PATENT DOCUMENTS

| | | |
|---|---|---|
| 3,359,331 A | 12/1967 | Baker et al. |
| 3,379,655 A | 4/1968 | May et al. |
| 3,455,995 A | 7/1969 | Bowman |
| 3,471,411 A | 10/1969 | Bowman et al. |
| 3,925,194 A | 12/1975 | Rodewald et al. .......... 208/109 |
| 4,188,311 A | 2/1980 | Aalbers et al. ............. 252/551 |
| 4,375,564 A | 3/1983 | Edwards ..................... 568/618 |
| 4,431,845 A | 2/1984 | Young et al. ............... 568/606 |
| 4,983,778 A | 1/1991 | Ploog ......................... 568/618 |
| 5,002,678 A | 3/1991 | Vanover et al. ............... 252/68 |
| 5,057,628 A | 10/1991 | Edwards et al. ............ 568/618 |
| 5,210,323 A | 5/1993 | Wimmer et al. ............ 568/615 |
| 5,292,986 A | 3/1994 | Abbott ....................... 585/730 |
| 5,391,722 A | 2/1995 | Chandalia et al. ......... 536/18.6 |
| 5,910,616 A | 6/1999 | Boyce et al. ............... 570/167 |

FOREIGN PATENT DOCUMENTS

| | | |
|---|---|---|
| EP | 0453967 A1 | 4/1991 |
| EP | 1002821 A1 | 5/2000 |
| GB | 796508 | 8/1955 |

OTHER PUBLICATIONS

Chemical Abstract CA 110:68525, 1989 no month available.*
Boron, Aluminum, and Gallium Tris(trifluoromethanesulfonate) (Triflate): Effective New Friedel–Crafts Catalysts, Olah, et al. J. Amer. Chem. Soc. 1988, 110, 2560–2565, no month available.
B. N. Chernyshov, N.S. Visilyuk, E.G. Il'sin, "Formation of Acidofluoro Complexes of Arsenic(V) and Antimony(V) in Aqueous–Organic and Peroxide Solutions," *Koordinatsionnaya Khimiya*, vol., 14, No. 10, pp. 1394–1399, Oct. 1988. (English Translation, Plenum Publishing, 1989) no month.

* cited by examiner

Primary Examiner—Elizabeth D. Wood

(57) ABSTRACT

Novel active catalyst compositions comprising a compound or mixture of compounds represented by the formula $$SbFX_mY_{4-m}$$

a complex of such a compound or mixture of such compounds being represented by the formula $$R \cdot SbFX_mY_{4-m}$$

or a combination of such compounds and complexes where in each formula, X is an anionic moiety, Y is an anion or anions resulting from the deprotonation of an active hydrogen-containing compound(s), m is 0 to 3 and R is one or more active hydrogen containing compound acting as molecules of solvation. The catalyst compositions are useful to promote alkoxylation reactions.

6 Claims, No Drawings

ANTIMONY CATALYST COMPOSITIONS

FIELD OF THE INVENTION

This invention relates to the preparation of highly active antimony catalyst compositions and the use of such catalyst compositions in chemical reactions including the selective addition reaction of an epoxide with an active hydrogen containing organic or inorganic compound, for example in the production of alkylene glycol ethers by the alkoxylation of lower alcohols with an alkylene oxide, to produce alkoxylated products.

BACKGROUND OF THE INVENTION

A variety of compounds have been proposed as catalysts for promoting addition reactions of epoxides and organic compounds containing active hydrogen. For example, the use of compounds which are basic in nature and are soluble in the reaction medium such as soluble basic salts of the alkali metals of Group I of the Periodic Table, e.g. sodium, potassium, rubidium and cesium, and of the alkaline earth metals of Group II of the Periodic Table, e.g. calcium, strontium and barium are well documented in the literature. Alkali metal hydroxides and alkoxides have long been used in the commercial production of glycol ethers. In general, these basic catalysts provide acceptably low by-product formation but when used in amounts sufficient to provide acceptable activity, the selectivity, i.e. the amount of monoalkoxylate produced as compared to the di-, tri- and higher alkoxylates produced, is somewhat deficient and could desirably be increased to improve process economics.

It is also well known that compounds having a strong acidic nature which are soluble in the reaction mixture can be used to catalyze the addition reaction of epoxides and hydroxylated compounds such as alcohols. For example, triflic acid and various soluble metal salts of triflic acid are described as catalysts for the alkoxylation reaction of alkanols and epoxides in U.S. Pat. No. 4,543,430 and Australian Patent No. 538,363.

Other acid compounds disclosed in the prior art as being useful to catalyze alkoxylation reactions include certain Lewis acid or Friedel-Crafts compounds. For example, in United Kingdom Patent 796,508 and in U.S. Pat. Nos. 3,359,331; 4,188,311; 4,983,778 and 5,057,628, antimony halides, in particular $SbCl_5$ are disclosed as being useful alkoxylation catalysts. U.S. Pat. No. 5,210,523 discloses the use of $SbBr_5$ and $SbCl_5$ complexed with certain Lewis bases as catalysts in alkoxylation reactions.

In general, the acid compounds disclosed in the prior art as useful alkoxylation catalysts are recognized as being highly active and providing excellent selectivity in producing a narrow range of alkoxylation products. However, corrosion and instability problems make many of these compounds difficult to use commercially and as a group, acid compounds, when used as alkoxylation catalysts, tend to promote side reactions leading to unacceptable levels of undesirable by-products being formed. Accordingly, industry continues to seek catalysts for the addition reaction of epoxides and organic or inorganic compounds, especially alcohols, that will provide a combination of high activity, good selectivity and minimal by-product formation.

SUMMARY OF THE INVENTION

According to the present invention, applicants have discovered that novel active catalyst compositions useful in a wide range of chemical reactions are obtained when certain fluorine containing antimony compounds (and/or their hydrogen, metal and ammonium salts) are reacted with active hydrogen-containing compounds. The resulting novel active catalyst compositions comprise a compound or mixture of compounds represented by the empirical formula $$SbFX_mY_{4-m}$$

wherein m is 0 to 3, a complex of such a compound or mixture of such compounds being represented by the empirical formula $$R \cdot SbFX_mY_{4-m}$$

wherein m is 0 to 3, or a combination thereof. In each formula, X is an anionic moiety and Y is an anion or anions resulting from the deprotonation of an active hydrogen-containing compound(s). When the catalyst is a complex or mixture of complexes, R is one or more neutral active hydrogen containing compound(s) acting as molecules of solvation and may include the compound(s) capable of being deprotonated to provide the anion Y.

The novel active catalyst compositions are useful generally in promoting chemical reactions and are uniquely effective in catalyzing the addition reaction of an epoxide and an organic or inorganic compound containing an active hydrogen, in particular alkanols, over a wide range of reaction temperatures and catalyst concentrations to obtain alkoxylation products at a high rate with excellent selectivity and remarkably low unwanted by-product formation compared to previously known catalysts.

DESCRIPTION OF THE INVENTION

The novel active catalyst compositions of the present invention comprise a compound or mixture of compounds represented by the empirical formula $$SbFX_mY_{4-m}$$

where m is 0 to 3, a complex of such a compound or mixture of complexed compounds being represented by the empirical formula $$R \cdot SbFX_mY_{4-m}$$

where m is 0 to 3, or a combination of such compounds and complexes. In each formula, X is an anionic moiety and Y is an anion or anions resulting from the deprotonation of an active hydrogen-containing compound(s). When the catalyst is a complex or mixture of complexes, R is one or more neutral active hydrogen containing compound(s) acting as molecules of solvation and may include the compound(s) capable of being deprotonated to provide the anion Y. Examples of X include fluorine, chlorine, bromine, iodine, sulfonates including tosylate, nosylate, mesylate, methane sulfonate and the like, cyanides, or mixtures thereof The novel catalyst compositions of the present invention are prepared by contacting at least one antimony precursor compound containing at least one fluorine, represented by the formula $$Sb(V)FX_4$$

and henceforth referred to as neutral catalyst precursors, wherein Sb(V) is antimony in a +5 oxidation state, X is an anionic moiety typically selected from the group comprising fluorine, chlorine, bromine, iodine, a sulfonate such as tosylate, nosylate, mesylate, methane sulfonate and the like, and a cyanide, or mixture thereof, or at least one salt thereof represented by the formula $$M^{n+}[Sb(V)FX_5]_n{}^{n-}$$

and henceforth referred to as ionic catalyst precursors, where $M^{n+}$ is selected from the group of hydrogen, ammonium, alkali, alkali earth and transition metals, or mixtures of such precursor compound and salt, where n is 1–4, with at least one active hydrogen containing compound, here represented by HY, under appropriate conditions of time and temperature to cause deprotonation of the active hydrogen containing compound and replacement of at least one, and up to all, of X in the precursor compound(s), via formation of HX, with anion Y resulting from such deprotonation. Particularly useful neutral catalyst precursor compounds are antimony pentafluoride and antimony pentahalides containing a mixture of fluoride and chloride. When ionic catalyst precursors are used, appropriate conditions of time and temperature to cause the dissociation of $M^{n+}(X^-)_n$ may precede the deprotonation of the active hydrogen containing compound to facilitate preparation of the active catalyst composition. Particularly useful ionic catalyst precursor compounds are hydrogen hexafluoroantimonate and hydrogen hexafluoroantimonate hexahydrate.

The active hydrogen containing compounds useful in preparing the catalyst compositions of the present invention include all compounds which are capable of undergoing deprotonation by the catalyst precursors at temperatures of from about 20° C. to about 200° C. at times typically ranging from from a few seconds to several days to yield an anion capable of replacing at least one X. Additionally, the active hydrogen containing compounds useful in preparing the catalyst compositions of the present invention may also act as a molecule or molecules of solvation to 1) the catalyst precursor compound or complex, and/or 2) the active catalyst composition of the present invention. Suitable active hydrogen containing compounds useful in the preparation of the active catalyst compositions of the present invention include, for example, water, primary, secondary and tertiary alcohols and thiols, carboxylic acids, substituted and unsubstituted phenols and thiophenols, bifunctional compounds such as catechols, diols, polyols and the analogous nitrogen containing compounds including primary and secondary amines, substituted and unsubstituted aryl amines, multifunctional amines such as ethylenediamine, diethylenetetraamine and phenylenediamine. Other hydrogen containing compounds which may be used include bifunctional compounds containing both nitrogen and oxygen or sulfur and oxygen or nitrogen and sulfur, for example 2-aminoethanol and 2-aminothiol and other ethanolamines. Hydrogen containing compounds which are mulifunctional and contain neutral functionalities which may interact beneficially with the active catalyst site may also be used, for example 2-alkoxyethanols, 2-(2-alkoxyethoxy)ethanols, orthoalkoxyphenols, 2-(2-tert-aminoethoxy)ethanols and ortho-tert-aminophenols. By way of illustration which is not intended to be limiting, suitable alcohols which may be useful in the preparation of the active catalyst compositions of the present invention include primary and secondary straight and branched chain alcohols containing up to 30 carbon atoms, cycloaliphatic alcohols, glycols, polyethylene glycols, polypropylene glycols and polyhydric alcohols such as pentaerythritol and glycerol. Particularly useful catalyst compositions can be obtained using primary and secondary straight and branched chain alcohols containing up to 30 carbon atoms. Furthermore, the active hydrogen containing compound may be the same as or different from the active hydrogen containing compound which is reacted with an epoxide in the alkoxylation reactions being promoted by the catalyst compositions of the present invention.

The catalyst compositions of the present invention are prepared by contacting the precursor compound or complex with the active hydrogen containing compound and heating the resulting mixture to an elevated temperature for sufficient time to form the active catalyst composition of the present invention. For neutral catalyst precursors, this transformation may be effected in short time periods, i.e., instantaneously to several minutes, at room temperature. The time and temperature required to effect this transformation for the ionic catalyst precursors may be greater than the time and temperature requirements for the neutral catalyst precursors due to the additional energy necessary to dissociate $M^{n+}(X^-)_n$ prior to the deprotonation of the active hydrogen containing reactant. Because of the variety of precursor compounds and complexes and active hydrogen containing compounds which may be reacted to produce the catalyst of the present invention, the temperature at which and time for which formation of the catalyst will occur will vary considerably within the ranges previously set forth. However, those of ordinary skill in the art will readily be able to optimize the appropriate reaction conditions for each combination of constituents by observing the quantity of HX liberated during the reaction. Preferably, the catalyst composition of this invention is prepared at a temperature of at least about 100° C.

Because the catalyst compositions of the present invention may be used in very low concentrations to effectively promote chemical reactions, low concentrations of catalyst precursors may be used in the preparation of the catalyst compositions resulting in very little HX being produced. Thus, for example in an alkoxylation reaction, the active catalyst composition may advantageously be formed in situ without the need to remove HX, since the amount of HX which is liberated during formation of the active catalyst composition of the present invention is not sufficient to be catalytically active in the alkoxylation reaction and does not promote formation of unwanted byproducts.

Certain neutral catalyst precursor compounds such as antimony pentafluoride are tetrameric in their pure form and very viscous. They are also extremely active and are advantageously dissolved in a suitable inert solvent which allows the tetramer to dissociate into monomers prior to introduction to the active hydrogen containing compounds. Perfluorinated hydrocarbons, such as perflouoroalkanes, perfluorodecalin, and perfluorobenzene are particularly useful as solvents since they break up the tetramer into its monomers, they do not undergo halogen exchange with these catalyst precursors and they provide a range of boiling points which are amenable to separation and removal from the active hydrogen containing compounds.

To avoid excessive reaction and heat generation upon initial contact with certain precursor compounds such as antimony pentafluoride, the active hydrogen containing compound should be cooled to a temperature below room temperature and as low as −100° C. if practical. After initial contact, the mixture of catalyst precursor compound, active hydrogen containing compound and inert solvent may be warmed to room temperature under vacuum in order to remove and recover the inert solvent. The resultant mixture of catalyst precursor compound and active hydrogen containing compound may then be heated to above room temperature to continue the formation of an active catalyst composition of the present invention. The ionic catalyst precursors are thought to be monomeric by virtue of stabilization by $M^{n+}(X^-)_n$. For this reason, they may be added directly to the active hydrogen containing compounds at room temperature. Additional energy is then required for the dissociation of $M^{n+}(X^-)_n$ to give an intermediate species resembling the neutral catalyst precursors which then react with the active hydrogen containing species to form the active catalyst compositions of the present invention.

The active catalyst composition of the present invention may be used in the alkoxylation of a wide variety of compounds containing active hydrogen including all of those listed above for use in preparing the active catalyst compositions of the present invention. Such compounds may include alcohols, phenols, carboxylic acids, amines and water. By way of illustration which is not intended to be limiting, suitable alcohols which may be alkoxylated using the process of the present invention include primary and secondary straight and branched chain alcohols containing up to 30 carbon atoms, cycloaliphatic alcohols, glycols, polyethylene glycols, polypropylene glycols and polyhydric alcohols such as pentaerythritol and glycerol. Alkoxylation of primary and secondary alcohols containing 1 to 15 carbon atoms represent a preferred embodiment of the alkoxylation process of the present invention. Particularly useful results have been demonstrated in the ethoxylation of a lower primary alkanol such as butanol to prepare ethylene glycol mono-primary alkyl ethers, ethoxylation of a lower secondary alcohol such as 4-methylpentan-2-ol to prepare ethylene glycol mono-secondary alkyl ethers, ethoxylation of water to prepare ethylene glycols, and the propoxylation of a lower primary alcohol such as butanol to prepare propylene glycol mono-primary alkyl ethers. The ethoxylation of secondary alcohols using the active catalyst composition of the present invention is particularly significant in that it results in much higher epoxide conversion and higher selectivity for the one mole ethoxylate than currently practiced technology.

Numerous epoxides including alkylene oxides, for example, oxides of internal and terminal aliphatic olefins, and oxides of epichlorohydrin may be used as a starting material in the alkoxylation process of the present invention. Examples of suitable epoxides include, without limitation, ethylene oxide, propylene oxide, butylene oxides, glycidol, epichlorohydrin, cyclohexene oxide, cyclopentene oxide and styrene oxide. With the antimony catalysts of the present invention, particularly useful results are achieved in alkoxylation reactions using ethylene oxide, propylene oxide and mixtures of ethylene oxide and propylene oxide.

Because of its high activity, the amount of active catalyst composition used to promote chemical reactions such as alkoxylation reactions, can be small relative to catalyst concentrations disclosed in prior art, and will vary depending on a number of factors including the particular catalyst species, temperature and other process conditions, the ratio of reactants and the desired balance of activity, selectivity and impurity formation sought by the skilled process operator. Typically, in alkoxylation reactions the concentration of active catalyst composition present may be in the range of 0.01 to 50,000 ppm antimony, based on the weight of the active hydrogen containing compound being alkoxylated, and more typically in the range of 0.1 to 500 ppm antimony. Excellent results have been obtained in alkoxylation reactions using active catalyst composition concentrations of less than 100 ppm antimony.

The temperature at which the process of the present invention may be carried out will also vary depending on a variety of factors such as equipment considerations, other process conditions such as catalyst concentration and reactor pressure and the desired activity and selectivity targeted by the process operator. Acceptable process operations may be conducted at a reactor temperature in the range of 60 to 240° C., more typically in the range of 100 to 200° C. It is a unique feature of the active catalyst compositions of the present invention that the production of unwanted by-products is low at low temperatures e.g., 120° C. or less and may actually decrease as the reaction temperature is increased to a temperature of 180° C. or higher.

The active catalyst compositions of the present invention may be prepared before addition to a chemical reactor or may be formed in situ in such reactor. For example, in an alkoxylation reaction, the active catalyst composition may be formed in situ by adding a solution of catalyst precursor compound to the active hydrogen containing compound to be alkoxylated in the reactor before or after addition of an epoxide compound and heating the reactor contents above room temperature.

Typically, catalyst precursor stock solutions will be prepared such that the effective antimony concentration, upon formation of the active catalyst composition of the present invention, is quantifiable. For example, in a preferred embodiment of the invention - the ethoxylation of butanol –2200 ppm $SbF_5$ or 3700 ppm $HSbF_6 \cdot 6H_2O$ in butanol give precursor stock solutions with an effective antimony concentration of ca. 1200–1300 ppm. These stock solutions are then mixed with the active hydrogen containing compound in a 100:1 compound to stock solution weight ratio, giving an effective antimony concentration of ca. 12–13 ppm. The precursor stock solutions are typically introduced when the hydrogen containing compound has reached a temperature sufficient to promote formation of the active catalyst composition.

In an embodiment of a commercial process for the ethoxylation of alcohols using the active catalyst compositions of the present invention, the alcohol may be continuously fed to a preheater/intercooler along with 5–40 wt. % ethylene oxide. This stream would be preheated prior to the addition of a metered continuous stream of catalyst precursor solution; the flow rate of the catalyst precursor solution would be controlled such that the total reactor feed would contain an effective antimony concentration of 5–100 ppm, depending upon the desired rate, selectivity and byproduct formation. Introduction of the catalyst precursor stream to the alcohol/ethylene oxide at the preheated temperature just prior to introduction to the reactor promotes immediate formation of the active catalytic species. Additional heat is provided by the exothermic nature of the ethoxylation reaction itself.

Preparation of the active catalyst compositions of the present invention and their use in alkoxylation reactions is further illustrated by the following examples.

EXAMPLE 1

Five active catalyst compositions of the present invention were prepared as follows:

CATALYST A 100 mL of BuOH was introduced to a 3-necked round bottomed flask under nitrogen purge and was cooled to −78° C. 2.17 g of $SbF_5$ dissolved in 10 mL of perfluorohexane was then added via syringe through a septum. The resulting solution was then allowed to warm to room temperature and remain there for one hour under a pressure of 30 mm of Hg in order to remove and recover the halogenated solvent. Vacuum and nitrogen purge were then removed and the solution was decanted into a glass bottle giving a 0.1 M stock solution of catalyst precursor.

To prepare an active catalyst composition of the present invention, 1 gram of the above stock solution was mixed with 9 grams of butanol and the mixture was added to 891 grams of butanol which had been heated to 180° C., whereby an active catalyst composition of the present invention having a concentration of 13 ppm antimony was formed instantaneously.

CATALYST B

The process for preparing CATALYST A was repeated except that the 1 gram of stock solution was mixed with 9 grams of butanol and the mixture was added to 891 grams of butanol which had been heated to 140° C. An active catalyst composition having a concentration of 13 ppm antimony was formed instantaneously.

CATALYST C

The process for preparing CATALYST A was repeated except that the 1 gram of stock solution was mixed with 9 grams of butanol and the mixture was added to 891 grams of butanol which had been heated to 100° C. An active catalyst composition having a concentration of 13 ppm antimony was formed instantaneously.

CATALYST D 100 mL of BuOH was introduced to a 3-necked round bottom flask under nitrogen purge. While maintaining the flask at room temperature 3.5 g of $HSbF_6 \cdot 6H_2O$ was added via syringe through a septum. The solution was then decanted into a glass bottle giving a 0.1 M stock solution.

To prepare the active catalyst composition of the present invention, 1 gram of the stock solution was mixed with 9 grams of butanol and the mixture was added to 891 grams of butanol which had been heated to 180° C., whereby an active catalyst composition of the present invention-having a concentration of 13 ppm antimony was formed instantaneously.

CATALYST E

The process for preparing CATALYST D was repeated except that the 1 gram of stock solution was mixed with 9 grams of butanol and the mixture was added to 891 grams of butanol which had been heated to 140° C. An active catalyst composition having a concentration of 13 ppm antimony was formed instantaneously.

EXAMPLE 2

To a 2L autoclave reactor equipped with a mechanical impeller, cooling coil, pressure transducer, vapor and liquid phase thermocouples, and various gas and sampling ports, 891 grams of butanol was charged. Once charged, the butanol was degassed with 50 psig of $N_2$ three times and 10 psig of $N_2$ was left in the reactor. The reactor contents were then brought up to a temperature of 180° C.

A liquid catalyst injection device was used to introduce catalyst precursor stock solution into the reactor. This device was charged with 1 g of the catalyst precursor stock solution used to prepared CATALYST A together with 9 g of butanol. The contents of the injection device were then introduced to the contents of the reactor which had been heated to a temperature of 180° C. resulting in the immediate formation of active catalyst having a concentration of 13 ppm antimony. 90 grams of ethylene oxide were then charged to the reactor via the oxide injector which was pressurized with 400 psig of $N_2$ to force the ethylene oxide into the reactor. The reaction temperature was maintained at 180° C.

The reaction run time was six times the reaction half life time which, in this example, was determined to be 4.92 minutes. The reaction half life is determined by measuring the time it takes for the pressure in the reactor to drop to one-half of the highest presssure achieved after addition of ethylene oxide and catalyst to the reactor. To shut down the reaction, the reactor heaters were turned off and full water flow to the cooling coils was initiated bringing the reaction mixture to room temperature. Once the reactor had cooled the contents were drained into a tared half gallon jug and a sample was removed for GC analysis. 183.92 grams of glycol ether product were obtained. Selectivity and by-product results are based on the results of the GC analysis of the of the reactor contents and are reported in Table 1.

EXAMPLE 3

Example 2 was repeated except that the quantity of catalyst precursor solution added to the reactor yeilded a concentration of catalyst in the reactor of 6 ppm. 182.84 grams of glycol ether product were obtained. Selectivity and by-product results are based on the results of the GC analysis of the of the reactor contents and are reported in Table 1.

EXAMPLE 4

Example 2 was repeated except that the contents of the reactor were heated to 140° C. and the reaction was run at a temperature of 140° C. 180.59 grams of glycol ether product were obtained. Selectivity and by-product results are based on the results of the GC analysis of the of the reactor contents and are reported in Table 1.

EXAMPLE 5

Example 2 was repeated except that the contents of the reactor were heated to 100° C. and the reaction was run at a temperature of 100° C. 186.96 grams of glycol ether product were obtained. Selectivity and by-product results are based on the results of the GC analysis of the of the reactor contents and are reported in Table 1.

EXAMPLE 6

Example 2 was repeated except that the liquid catalyst injection device was charged with 1 gram of the precursor stock solution used to prepare CATALYST D together with 9 grams of butanol. The quantity of catalyst precursor solution added to the reactor yeilded a concentration of catalyst in the reactor of 13 ppm. 173.59 grams of glycol ether product were obtained. Selectivity and by-product results are based on the results of the GC analysis of the of the reactor contents and are reported in Table 1.

EXAMPLE 7

Example 6 was repeated except that the contents of the reactor were heated to 140° C. and the reaction was run at a temperature of 140° C. 183.16 grams of glycol ether product were obtained. Selectivity and by-product results are based on the results of the GC analysis of the of the reactor contents and are reported in Table 1.

EXAMPLE 8

Example 7 was repeated using triflic acid (HOTf) as the catalyst at a concentration of 16 ppm in the reactor. 216.78 grams of glycol ether product were obtained. Selectivity and by-product results are based on the results of the GC analysis of the of the reactor contents and are reported in Table 1.

EXAMPLE 9

Example 8 was repeated except that the a reaction was carried out at a temperature of 100° C. 216.40 grams of glycol ether product were obtained. Selectivity and by-product results are based on the results of the GC analysis of the of the reactor contents and are reported in Table 1.

TABLE 1

| Exam | Catalyst Conc. | Reaction Temp. | Half Life | Selectivity (1) | By-products (2) |
|---|---|---|---|---|---|
| 2 | 13 ppm | 180° C. | 4.92 min | 15.36 | 0.10% |
| 3 | 6 ppm | 180° C. | 19.91 min | 16.07 | 0.088% |
| 4 | 13 ppm | 140° C. | 9.90 min | 14.72 | 0.18% |
| 5 | 13 ppm | 100° C. | 13.3 min | 10.0 | 0.42% |
| 6 | 13 ppm | 180° C. | 7.75 min | 15.95 | 0.012% |
| 7 | 13 ppm | 140° C. | 27.66 min | 14.61 | 0.16% |
| 8 | 16 ppm | 180° C. | 4.0 min | 8.9 | 1.56% |
| 9 | 16 ppm | 100° C. | 40.15 min | 7.4 | 0.31% |

(1) Ratio of one mole adduct to two mole adduct.
(2) By-products as wt. % of products.

The data in Table 1 clearly shows that the catalyst compositions of the present invention represented by Examples 2 to 7 exhibit equal or better activity and far superior selectivity with significantly less unwanted by-product formation at higher reaction temperatures when compared to triflic acid, a known strong protic acid alkoxylation catalyst, represented in Examples 8 and 9.

EXAMPLE 10

To a 2L autoclave equipped with a mechanical impeller, cooling coil, pressure transducer, vapor and liquid phase thermocouples, and various gas and sampling ports, 891 grams of water was charged. Once charged, the water was degassed with 50 psig of $N_2$ three times and 10 psig of $N_2$ was left in the reactor. The reactor contents were then brought up to a temperature of 120° C.

The catalyst injection device used in Example 2 was charged with 10 g of $1 \times 10^{-2}$ M aqueous $HSbF_6$. The contents of the device were introduced to the contents of the reactor which had been heated to 120° C. to provide an active catalyst composition having a concentration of 13 ppm antimony. 90 grams of ethylene oxide was then charged to the reactor via the oxide injector which was pressurized with 400 psig of $N_2$ to force the ethylene oxide into the reactor. The reaction temperature was maintained at 120° C.

The reaction run time was six times the reaction half life time which in this example was determined to be 3.09 minutes. On shut down the heaters were turned off and full water flow to the cooling coils was initiated to bring the reaction mixture to room temperature. Once the reactor had cooled, the contents were drained into a tared half gallon jug and a sample was removed for GC analysis. Conversion to ethylene glycol products was 100% based on ethylene oxide. 981 grams of glycol products were obtained. Product selectivity measured as the ratio of ethylene glycol to diethylene glycol was determined to be 11.8 and the product had no detectable unwanted by-products.

EXAMPLE 11

Example 2 was repeated except that 4-methylpentan-2-ol was substituted for butanol in the catalyst injector device and the reactor. 74 grams of ethylene oxide were added to the reactor. The reaction run time was six times the reaction half life time which in this example was determined to be 16.83 minutes. 154.99 grams of glycol ether product were produced. Selectivity measured as the ratio of monoethylene glycol ether to diethylene glycol ether was determined to be 3.1.

EXAMPLE 12

Example 2 was repeated except that 119 grams of propylene oxide was used in place of the ethylene oxide and was added to,the reactor with 891 grams of butanol prior to heat up. The reaction run time was 67 minutes. 186.19 grams of glycol ether product was obtained. Selectivity of the product obtained, measured as the ratio of monopropylene glycol ether to dipropylene glycol ether was determined to be 15.

What is claimed is:

1. An active catalyst composition comprising a compound or a mixture of compounds represented by the formula $$SbFX_mY_{4-m}$$

a complex of such a compound or a mixture of complexed compounds being represented by the formula $$R-SbFX_mY_{4-m}$$

or a combination of such compounds and complexes wherein each formula X is an anionic moiety, Y is an anion or anions resulting from the deprotonation of an active hydrogen containing compound(s), m is 0 to 3, R is one or more neutral active hydrogen containing compounds acting as molecules of solvation; the composition being prepared at a temperature of at least about 100° C.

2. The catalyst composition of claim 1 wherein X is selected from the group consisting of fluorine, chlorine, bromine, iodine, sulfonates and cyanides or mixtures thereof.

3. The catalyst composition of claim 2 wherein X is fluorine or a mixture of fluorine and chlorine.

4. The catalyst composition of claim 1 wherein Y is an anion resulting from the deprotonation of a primary or secondary branched or straight chain alcohol containing up to 30 carbon atoms or mixtures thereof.

5. A process for preparing an active catalyst composition which comprises contacting at least one neutral antimony precursor compound containing at least one fluorine, represented by the formula $$Sb(V)FX_4$$

wherein Sb(V) is antimony in the +5 oxidation state and X is an anionic moiety, or a salt thereof represented by the formula $$M^{n+}[Sb(V)FX_5]_n^{n-}$$

wherein $M^{n+}$ is selected from the group of hydrogen, ammonium, alkali, alkali earth and transition metals and n is 1 to 4, or mixtures of such neutral antimony precursor compounds(s) and salts thereof, with an active hydrogen containing compound, at a temperature of at least about 100° C.

6. An active catalyst composition comprising a compound or a mixture of compounds represented by the formula $$SbFX_mY_{4-m}$$

a complex of such a compound or a mixture of complexed compounds being represented by the formula $$R-SbFX_mY_{4-m}$$

or a combination of such compounds and complexes wherein each formula X is an anionic moiety, Y is an anion or anions resulting from the deprotonation of an active hydrogen containing compound(s), m is 0 to 3, R is one or more neutral active hydrogen containing compounds acting as molecules of solvation, prepared by the process comprising contacting at least one neutral antimony precursor compound containing at least one fluorine, represented by the formula $$Sb(V)FX_4$$

wherein Sb(V) is antimony in the +5 oxidation state and X is an anionic moiety, or a salt thereof represented by the formula $$M^{n+}[Sb(V)FX_5]_n^{n-}$$

wherein $M^{n+}$ is selected from the group of hydrogen, ammonium, alkali, alkali earth and transition metals and n is 1 to 4, or mixtures of such neutral antimony precursor compounds(s) and salts thereof, with an active hydrogen containing compound, at a temperature of at least about 100° C.

* * * * *